(12) United States Patent
Nishiguchi et al.

(10) Patent No.: US 6,410,574 B2
(45) Date of Patent: Jun. 25, 2002

(54) FUNGICIDAL COMPOSITION AND METHOD FOR USING THE SAME

(75) Inventors: Tsutomu Nishiguchi; Tsuyoshi Takemoto, both of Kawachinagano; Sohkichi Tajima, Osaka; Yoshinobu Yamamoto, Kawachinagano, all of (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 09/362,087

(22) Filed: Jul. 28, 1999

(30) Foreign Application Priority Data

Jul. 30, 1998 (JP) .......................... 10-229403

(51) Int. Cl.$^7$ ..................... A01N 43/828; A01N 37/00; A01N 43/00; A01N 47/00; A01N 55/02

(52) U.S. Cl. .................. 514/361; 514/267; 514/269; 514/291; 514/314; 514/359; 514/360; 514/383; 514/384; 514/396; 514/398; 514/400; 514/439; 514/440; 514/443; 514/447; 514/463; 514/468; 514/479; 514/480; 514/482; 514/500; 514/539; 514/562; 514/567; 514/570; 514/614

(58) Field of Search .................. 514/359, 360, 514/361, 267, 269, 291, 314, 383, 384, 396, 398, 400, 439, 440, 443, 447, 463, 468, 479, 480, 482, 500, 539, 562, 567, 570, 614

(56) References Cited

U.S. PATENT DOCUMENTS 4,314,839 A * 2/1982 Kruger et al. .............. 504/170

FOREIGN PATENT DOCUMENTS

| EP | 0 098 468 | 1/1984 |
| EP | 0098486 | 1/1984 |
| EP | 0 930 305 | 7/1999 |
| EP | 0 930 306 | 7/1999 |
| JP | 8-325110 A | 4/1997 |
| WO | WO 96/29871 | 10/1996 |

OTHER PUBLICATIONS

Patent Abstract, JP8–324110, Dec. 1996.

* cited by examiner

*Primary Examiner*—Jose' G. Dees
*Assistant Examiner*—Frank Choi
(74) *Attorney, Agent, or Firm*—Manelli Denison & Selter PLLC; Paul E. White, Jr.

(57) ABSTRACT

The present invention relates to a fungicidal composition obtained by mixing a 1,2,3-thiadiazole derivative of general formula (I) useful as a plant disease controller with at least one fungicide selected from the compounds having a fungicidal activity against plant diseases, and to a method for using the same:

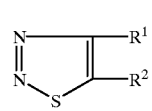

(I)

wherein $R^1$ is hydrogen, alkyl or cycloalkyl and $R^2$ is CO—Y—$R^3$, wherein Y is O, S, $NR^4$ or the like and $R^3$ is hydrogen, alkyl, phenyl, 5- or 6-membered heterocycle or the like.

3 Claims, No Drawings

FUNGICIDAL COMPOSITION AND METHOD FOR USING THE SAME

BACKGROUND OF THE INVENTION

1. Field of the Invention

The present invention relates to a fungicidal composition obtained by mixing a 1,2,3-thiadiazole derivative represented by general formula (I) useful as a plant disease controller with at least one fungicides selected from the compounds having a fungicidal activity against plant diseases, and a method for using the same.

2. Related Art

Although some of the 1,2,3-thiadiazole derivatives represented by the general formula (I) are novel compounds, many of such derivatives are disclosed in JP-A 8-325110 which mentions usefulness of these compounds as a plant disease controller. On the other hand, the compounds constituting the other ingredient of the composition of the present invention which are compounds having a fungicidal activity against plant diseases are known fungicides disclosed in literature.

SUMMARY OF THE INVENTION

With the aim of further decreasing the dosage of 1,2,3-thiadiazole derivatives, the present inventors attempted a combined use of the 1,2,3-thiadiazole derivatives with a variety of known fungicides. As a result, it was found that an effect unexpectable from their single use could be exhibited by such a combined use. Based on this finding, the present invention was accomplished.

It was further found that an excellent effect unexpectable from foliage treatment could be exhibited by treating the seeds or the cultivation carrier used for seeding with a combination of a 1,2, 3-thiadiazole derivative and other fungicides. Based on this finding, the present invention was accomplished.

DETAILED DESCRIPTION OF THE INVENTION

The present invention relates to a fungicidal composition comprising, as active ingredients thereof, a 1,2,3-thiadiazole derivative represented by the following general formula (I) and at least one compound selected from the compounds having a fungicidal activity against plant diseases, and to a method for using the same:

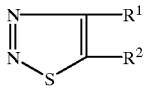

(I)

wherein $R^1$ represents hydrogen atom, $(C_{1-6})$ alkyl group or $(C_{3-7})$ cycloalkyl group; and $R^2$ represents a group of the formula:

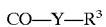

CO—Y—$R^3$ wherein $R^3$ represents hydrogen atom, $(C_{1-20})$ alkyl group, halo $(C_{1-20})$ alkyl group, $(C_{2-20})$ alkenyl group, halo $(C_{2-20})$ alkenyl group, $(C_{2-20})$ alkynyl group, halo $(C_{2-20})$ alkynyl group, $(C_{3-12})$ cycloalkyl group, $(C_{1-6})$ alkoxy $(C_{1-6})$ alkyl group, $(C_{1-6})$ alkoxy $(C_{1-6})$alkoxy $(C_{1-6})$ alkyl group, carboxyl $(C_{1-6})$ alkyl group, $(C_{1-20})$ alkoxycarbonyl $(C_{1-6})$ alkyl group, carbamoyl (C1-6) alkyl group, substituted carbamoyl $(C_{1-6})$ alkyl group having 1 or 2, same or different substituents selected from the group consisting of $(C_{1-6})$ alkyl group, phenyl group and substituted phenyl group substituted with at least one same or different halogen atom or $(C_{1-6})$ alkyl group, cyano $(C_{1-6})$ alkyl group, $(C_{1-6})$ alkylcarbonyloxy $(C_{1-6})$ alkyl group, $(C_{1-6})$ alkylcarbonylamino (C1-6) alkyl group, phenyl group, substituted phenyl group having 1 to 5, same or different substituents selected from the group consisting of halogen atom, hydroxyl group, cyano group, nitro group, (C1-6) alkyl group, halo $(C_{1-6})$ alkyl group, $(C_{1-6})$ alkoxy group, halo (C1-6) alkoxy group, carboxyl group, $(C_{1-12})$ alkoxycarbonyl group, carbamoyl group and substituted carbamoyl group having 1 or 2, same or different substituents selected from the group consisting of halogen atom, $(C_{1-12})$ alkyl group, phenyl group and substituted phenyl group substituted with 1 to 5, same or different $(C_{1-6})$ alkyl groups, phenyl $(C_{1-6})$ alkyl group, substituted phenyl $(C_{1-6})$ alkyl group having, on the ring thereof, 1 to 5, same or different substituents selected from the group consisting of halogen atom, hydroxyl group, cyano group, nitro group, $(C_{1-6})$ alkyl group, halo $(C_{1-6})$ alkyl group, $(C_{1-6})$ alkoxy group, halo $(C_{1-6})$ alkoxy group, carboxyl group, $(C_{1-12})$ alkoxycarbonyl group, carbamoyl group and substituted carbamoyl group having 1 or 2, same or different substituent selected from the group consisting of halogen atom, (C1-12) alkyl group, phenyl group and substituted phenyl group substituted with 1 to 5, same or different $(C_{1-6})$ alkyl groups, phenylcarbonyloxy $(C_{1-6})$ alkyl group, substituted phenylcarbonyloxy $(C_{1-6})$ alkyl group having, on the ring thereof, 1 to 5, same or different substituents selected from the group consisting of halogen atom, hydroxyl group, cyano group, nitro group, $(C_{1-6})$ alkyl group, halo (C1-6) alkyl group, $(C_{1-6})$ alkoxy group, halo $(C_{1-6})$ alkoxy group, carboxyl group, (C1-12) alkoxycarbonyl group, carbamoyl group and substituted carbamoyl group having 1 or 2, same or different substituents selected from the group consisting of halogen atom, $(C_{1-12})$ alkyl group, phenyl group and substituted phenyl group substituted with 1 to 5, same or different $(C_{1-6})$ alkyl groups, phenylcarbonyl $(C_{1-6})$ aminoalkyl group, substituted phenylcarbonyl $(C_{1-6})$ aminoalkyl group having, on the ring thereof, 1 to 5, same or different substituents selected from the group consisting of halogen atom, hydroxyl group, cyano group, nitro group, $(C_{1-6})$ alkyl group, halo $(C_{1-6})$ alkyl group, $(C_{1-6})$ alkoxy group, halo $(C_{1-6})$ alkoxy group, carboxyl group, $(C_{1-12})$ alkoxycarbonyl group, carbamoyl group and substituted carbamoyl group having 1 or 2, same or different substituents selected from the group consisting of halogen atom, $(C_{1-12})$ alkyl group, phenyl group and substituted phenyl group substituted with 1 to 5, same or different $(C_{1-6})$ alkyl groups, 5- or 6-membered heterocycle having at least one same or different heteroatoms selected from the group consisting of oxygen atom, sulfur atom and nitrogen atom, substituted 5-or 6-membered heterocycle having 1 to 5 same or different substituents selected from the group consisting of halogen atom, hydroxyl group, cyano group, nitro group, $(C_{1-6})$ alkyl group, halo $(C_{1-6})$ alkyl group, $(C_{1-6})$ alkoxy group, halo $(C_{1-6})$ alkoxy group, carboxyl group, $(C_{1-12})$ alkoxycarbonyl group, carbamoyl group and substituted carbamoyl group having 1 or 2, same or different substituents selected from the group consisting of halogen atom, $(C_{1-12})$ alkyl group, phenyl group and substituted phenyl group substituted with 1 to 5, same or different (C 16) alkyl groups, 5- or 6-membered heterocycle $(C_{1-6})$ alkyl group having at least one same or different heteroatoms selected from the group consisting of oxygen atom, sulfur atom and nitrogen atom, substituted 5- or 6-membered heterocycle $(C_{1-6})$ alkyl group having 1 to 5, same or different substituents selected from the group consisting of halogen atom, hydroxyl group, cyano group, nitro group, ($C_{1-6}$) alkyl group, halo ($C_{1-6}$) alkyl group, ($C_{1-6}$) alkoxy group, halo ($C_{1-6}$) alkoxy group, carboxyl group, ($C_{1-12}$) alkoxycarbonyl group, carbamoyl group and substituted carbamoyl group having 1 or 2, same or different substituents selected from the group consisting of halogen atom, ($C_{1-12}$) alkyl group, phenyl group and substituted phenyl group substituted with 1 to 5, same or different ($C_{1-6}$) alkyl groups, 5- or 6-membered heterocycle carbonyloxy ($C_{1-6}$) alkyl group having at least one, same or different heteroatoms selected from the group consisting of oxygen atom, sulfur atom and nitrogen atom, substituted 5- or 6-membered heterocycle carbonyloxy ($C_{1-6}$) alkyl group having 1 to 5, same or different substituents selected from the group consisting of halogen atom, hydroxyl group, cyano group, nitro group, ($C_{1-6}$) alkyl group, halo ($C_{1-6}$) alkyl group, (($C_{1-6}$) alkoxy group, halo ($C_{1-6}$) alkoxy group, carboxyl group, ($C_{1-12}$) alkoxycarbonyl group, carbamoyl group and substituted carbamoyl group having 1 or 2, same or different substituents selected from the group consisting of halogen atom, ($C_{1-12}$) alkyl group, phenyl group and substituted phenyl group substituted with 1 to 5, same or different ($C_{1-6}$) alkyl groups, 5- or 6-membered heterocycle carbonylamino ($C_{1-6}$) alkyl group having at least one same or different heteroatoms selected from the group consisting of oxygen atom, sulfur atom and nitrogen atom, substituted 5-or 6-membered heterocycle carbonylamino ($C_{1-6}$) alkyl group having 1 to 5, same or different substituents selected from the group consisting of halogen atom, hydroxyl group, cyano group, nitro group, ($C_{1-6}$) alkyl group, halo ($C_{1-6}$) alkyl group, ($C_{1-6}$) alkoxy group, halo ($C_{1-6}$) alkoxy group, carboxyl group, ($C_{1-12}$) alkoxycarbonyl group, carbamoyl group and substituted carbamoyl group substituted with 1 or 2, same or different substituents selected from halogen atom, ($C_{1-12}$) alkyl group, phenyl group and substituted phenyl group substituted with 1 to 5, same or different ($C_{1-6}$) alkyl groups, or a group of the formula:

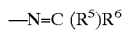

—N=C ($R^5$)$R^6$ wherein $R^5$ and $R^6$, same or different each other, represent hydrogenatom, ($C_{1-6}$) alkyl group, halo ($C_{1-6}$) alkyl group, ($C_{3-6}$) cycloalkyl group, phenyl group or substituted phenyl group substituted with same or different substituents selected from the group consisting of halogen atom, ($C_{1-6}$) alkyl group and ($C_{1-6}$) alkoxy group, or $R^5$ and $R^6$ may also be taken conjointly to represent ($C_{2-6}$) alkylene group which may be intercepted by O, S or $NR^4$ in which $R^4$ is hydrogen atom or ($C_{1-6}$) alkyl group; and Y represents O, S or $NR^4$ in which $R^4$ is as defined above, or a group of the formula:

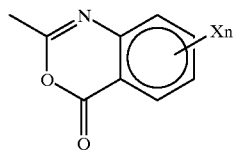

wherein X, same or different, represents halogen atom, hydroxyl group, cyano group, nitro group, ($C_{1-6}$) alkyl group, halo ($C_{1-6}$) alkyl group, ($C_{1-6}$) alkoxy group, halo ($C_{1-6}$) alkoxy group, ($C_{1-6}$) alkylcarbonyl group, carboxyl group, ($C_{1-12}$) alkoxycarbonyl group, carbamoyl group and substituted carbamoyl group having 1 or 2 same or different substituents selected from the group consisting of halogen atom, ($C_{1-12}$) alkyl group, phenyl group and substituted phenyl group substituted with 1 to 5, same or different ($C_{1-6}$) alkyl groups; and n represents an integer of 0 to 4.

The present invention provides fungicidal compositions which can be used at a low dosage of 1,2,3-thiadiazole derivative represented by the general formula (I). These compositions have an excellent activity as a fungicide. The present invention further provides a more effective method for using the fungicidal composition which comprises applying the active ingredient or the fungicide containing the same to seeds or plants in the seedling period. The use of said composition or said method for using the composition makes it possible to stabilize the fungicidal effect and to inhibit generation of agent-resistant fungi.

The 1,2,3-thiadiazole derivatives represented by the general formula (I) constitute the other active ingredient of the composition of the present invention, of which typical examples are listed in Tables 1 and 3. The present invention is by no means limited by these examples.

General formula (I-1)

TABLE 1

(I-1)

| No. | $R^1$ | Y | $R^3$ | Properties |
|---|---|---|---|---|
| 1 | H | O | H | m.p. 107.1° C. |
| 2 | H | NH | H | m.p. 160.8° C. |
| 3 | $CH_3$ | O | H | m.p. 188–189.5° C. |
| 4 | $CH_3$ | O | Na | m.p. 230° C. (decomposition) |
| 5 | $CH_3$ | O | $CH_3$ | nD 1.5165 (23.2° C.) |
| 6 | $CH_3$ | O | $C_2H_5$ | nD 1.5075 (14.0° C.) |
| 7 | $CH_3$ | O | n-$C_3H_7$ | nD 1.4000 (12.5° C.) |
| 8 | $CH_3$ | O | i-$C_3H_7$ | nD 1.4400 (14.3° C.) |
| 9 | $CH_3$ | O | s-$C_4H_9$ | nD 1.4165 (24.2° C.) |
| 10 | $CH_3$ | O | $CH_2CH(C_2H_5)C_4H_9$-n | nD 1.4891 (23.1° C.) |
| 11 | $CH_3$ | O | n-$C_8H_{17}$ | nD 1.4900 (12.9° C.) |
| 12 | $CH_3$ | O | n-$C_{12}H_{25}$ | nD 1.5403 (22.0° C.) |
| 13 | $CH_3$ | O | n-$C_{16}H_{33}$ | nD 1.4859 (22.0° C.) |

TABLE 1-continued (I-1)

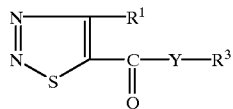

| No. | R¹ | Y | R³ | Properties |
|---|---|---|---|---|
| 14 | $CH_3$ | O | $c\text{-}C_6H_{11}$ | nD 1.5248 (25.2° C.) |
| 15 | $CH_3$ | O | $CH_2$—Ph | nD 1.5735 (13.1° C.) |
| 16 | $CH_3$ | O | $CH_2$-(4-Cl—Ph) | m.p. 85° C. |
| 17 | $CH_3$ | O | $CH_2$-(3,5-$Cl_2$—Ph) | m.p. 81° C. |
| 18 | $CH_3$ | O | $CH_2$-(4-t-$C_4H_9$—Ph) | nD 1.5558 (26.3° C.) |
| 19 | $CH_3$ | O | $CH_2$-(4-$NO_2$—Ph) | m.p. 100° C. |
| 20 | $CH_3$ | O | $CH(CH_3)$—Ph | nD 1.5631 (25.0° C.) |
| 21 | $CH_3$ | O | Ph | nD 1.5845 (20.6° C.) |
| 22 | $CH_3$ | O | 4-Cl—Ph | m.p. 77–80° C. |
| 23 | $CH_3$ | O | 2-$CH_3$—Ph | m.p. 62–64° C. |
| 24 | $CH_3$ | O | 4-$CH_3$—Ph | m.p. 31° C. |
| 25 | $CH_3$ | O | 4-$CH_3O$—Ph | m.p. 73° C. |
| 26 | $CH_3$ | O | 2-$COCH_3$ | m.p. 77° C. |
| 27 | $CH_3$ | O | 2-$COOCH_3$—Ph | m.p. 102° C. |
| 28 | $CH_3$ | O | 2-$COOC_3H_7$-i | Paste |
| 29 | $CH_3$ | O | $CH_2$—$Q^1$ | nD 1.5391 (17.1° C.) |
| 30 | $CH_3$ | O | $CH_2CH_2O$—$Q_2$ | m.p. 54° C. |
| 31 | $CH_3$ | O | $CH_2CH(CH_3)O$—$Q_2$ | nD 1.5812 (22° C.) |
| 32 | $CH_3$ | O | (s)-$CH(CH_3)COOC_2H_5$ | nD 1.4858 (21.9° C.) |
| 33 | $CH_3$ | O | $CH_2CH_2NHCO$—Ph | m.p. 85° C. |
| 34 | $CH_3$ | O | N=CH—Ph | m.p. 113.5° C. |
| 35 | $CH_3$ | O | N=C($CH_3$)Ph | m.p. 99.9° C. |
| 36 | $CH_3$ | S | $CH_3$ | m.p. 40.1° C. |
| 37 | $CH_3$ | S | $C_2H_5$ | nD 1.5229 (20.8° C.) |
| 38 | $CH_3$ | S | $i\text{-}C_3H_7$ | nD 1.5620 (21.8° C.) |
| 39 | $CH_3$ | S | $n\text{-}C_{12}H_{25}$ | nD 1.5621 (18.6° C.) |
| 40 | $CH_3$ | S | $CH_2$—Ph | nD 1.6239 (21.1° C.) |
| 41 | $CH_3$ | NH | H | m.p. 115° C. |
| 42 | $CH_3$ | NH | $CH_3$ | m.p. 45° C. |
| 43 | $CH_3$ | NH | $C_2H_5$ | m.p. 44° C. |
| 44 | $CH_3$ | NH | $i\text{-}C_3H_7$ | m.p. 65° C. |
| 45 | $CH_3$ | NH | $c\text{-}C_6H_{11}$ | m.p. 98° C. |
| 46 | $CH_3$ | NH | Ph | m.p. 110° C. |
| 47 | $CH_3$ | NH | 2-Cl—Ph | m.p. 101° C. |
| 48 | $CH_3$ | NH | 3-Cl—Ph | m.p. 136–142° C. |
| 49 | $CH_3$ | NH | 4-Cl—Ph | m.p. 114° C. |
| 50 | $CH_3$ | NH | 2-$CH_3$—Ph | m.p. 115° C. |
| 51 | $CH_3$ | NH | 3-$CH_3$—Ph | m.p. 111° C. |
| 52 | $CH_3$ | NH | 4-$CH_3$—Ph | m.p. 109° C. |
| 53 | $CH_3$ | NH | 2,4-$Cl_2$—Ph | m.p. 118–119° C. |
| 54 | $CH_3$ | NH | 3,4-$Cl_2$—Ph | m.p. 138–139° C. |
| 55 | $CH_3$ | NH | 3-Cl-4-$CH_3$—Ph | m.p. 113° C. |
| 56 | $CH_3$ | NH | 3,4-$(CH_3)_2$—Ph | m.p. 111° C. |
| 57 | $CH_3$ | NH | 4-$CH_3O$—Ph | m.p. 117° C. |
| 58 | $CH_3$ | NH | 4-$NO_2$—Ph | m.p. 175° C. |
| 59 | $CH_3$ | NH | 4-CN—Ph | m.p. 172° C. |
| 60 | $CH_3$ | NH | 2-COOH—Ph | m.p. 223° C. |
| 61 | $CH_3$ | NH | 2-$COOC_2H_5$—Ph | m.p. 63° C. |
| 62 | $CH_3$ | NH | 4-$COOCH_3$—Ph | m.p. 133° C. |
| 63 | $CH_3$ | NH | 2-$CONHCH_3$—Ph | m.p. 162° C. |
| 64 | $CH_3$ | NH | 2-$CONHC_3H_7$-i-Ph | m.p. 177° C. |
| 65 | $CH_3$ | NH | 3-$CONHC_3H_7$-i-Ph | m.p. 158° C. |
| 66 | $CH_3$ | NH | 4-$CON(CH_3)_2$—Ph | m.p. 176.8–178.6° C. |
| 67 | $CH_3$ | NH | $CH_2$—Ph | m.p. 53° C. |
| 68 | $CH_3$ | NH | $CH(CH_3)$ (4-Cl—Ph) | m.p. 108° C. |
| 69 | $CH_3$ | NH | $CH_2CN$ | m.p. 76–78° C. |
| 70 | $CH_3$ | NH | $CH_2CH_2CN$ | m.p. 86–87° C. |
| 71 | $CH_3$ | NH | $CH(CH_3)$ ($i\text{-}C_3H_7$) | nD 1.5235 (25.9° C.) |
| 72 | $CH_3$ | NH | $CH_2COOC_2H_5$ | nD 1.5248 (21.5° C.) |
| 73 | $CH_3$ | NH | $CH_2COOC_8H_{17}$-n | Paste |
| 74 | $CH_3$ | NH | $CH_2CONH$(4-Cl—Ph) | m.p. 211° C. |
| 75 | $CH_3$ | NH | $CH_2CONH$(4-$CH_3O$—Ph) | m.p. 188° C. |
| 76 | $CH_3$ | NH | $CH(CH_3)CH_2COOCH_3$ | nD 1.5250 (20.4° C.) |
| 77 | $CH_3$ | NH | $CH(i\text{-}C_3H_7)COOCH_3$ | Paste |
| 78 | $CH_3$ | NH | $CH(CH_3)COOCH_3$ | Paste |
| 79 | $CH_3$ | NH | $CH_2CH_3NHCOQ^2$ | m.p. 149° C. |

TABLE 1-continued (I-1)

$$\text{structure with } R^1, C\text{-}Y\text{-}R^3, O$$

| No. | R¹ | Y | R³ | Properties |
|---|---|---|---|---|
| 80 | CH₃ | NH | N=C(CH₃)₂ | m.p. 198° C. |
| 81 | CH₃ | NH | N=C(CH₃)C₂H₅ | m.p. 152–153° C. |
| 82 | CH₃ | NH | N=CH—Ph | m.p. 238° C. |
| 83 | CH₃ | NH | N=C(CH₃)—Ph | m.p. 260–270° C. |
| 84 | CH₃ | NCH₃ | CH₃ | nD 1.5555 (13.2° C.) |
| 85 | CH₃ | NC₂H₅ | C₂H₅ | nD 1.5356 (13.7° C.) |
| 86 | C₂H₅ | O | H | m.p. 137.1–138.4° C. |
| 87 | C₂H₅ | O | CH₃ | nD 1.5093 (24.1° C.) |
| 88 | C₂H₅ | O | CH₂—Ph | nD 1.5539 (23.7° C.) |
| 89 | C₂H₅ | NH | H | m.p. 139.0° C. |
| 90 | C₂H₅ | NH | Ph | m.p. 81.9° C. |
| 91 | n-C₃H₇ | O | C₂H₅ | nD 1.4958 (21.0° C.) |
| 92 | i-C₃H₇ | O | H | m.p. 136.6° C. |
| 93 | i-C₃H₇ | O | C₂H₅ | nD 1.4943 (20.9° C.) |
| 94 | i-C₃H₇ | O | n-C₈H₁₇ | nD 1.4845 (21.8° C.) |
| 95 | i-C₃H₇ | O | CH₂—Ph | nD 1.5505 (23.8° C.) |
| 96 | i-C₃H₇ | NH | H | m.p. 137.3° C. |
| 97 | i-C₃H₇ | NH | Ph | m.p. 112.3° C. |
| 98 | n-C₄H₉ | O | H | m.p. 92.3° C. |
| 99 | n-C₄H₉ | O | CH₃ | nD 1.4993 (22.3° C.) |
| 100 | t-C₄H₉ | O | H | m.p. 111.1° C. |
| 101 | t-C₄H₉ | O | CH₃ | nD 1.5082 (13.0° C.) |
| 102 | n-C₅H₁₁ | O | H | m.p. 86.2° C. |
| 103 | n-C₅H₁₁ | O | CH₃ | nD 1.4969 (22.5° C.) |
| 104 | c-C₃H₅ | O | H | m.p. 157.1° C. |
| 105 | c-C₃H₅ | O | CH₃ | m.p. 47.4° C. |

In Table 1, "Ph" represents a phenyl group, "c—" represents an alicyclic hydrocarbon group, and $Q^1$ and $Q^2$ represent the following groups, respectively:

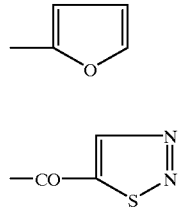

Some of the compounds shown in Table 1 are in the state of a paste, of which NMR values are shown in Table 2.

TABLE 2

| No. | ¹H-NMR[CDCl₃/TMS, δ value (ppm)] |
|---|---|
| 73 | 0.88(t, 3H), 1.21–1.40(m, 10H), 1.60–1.74(m, 2H), 2.94(s, 3H), 4.18–4.24(m, 4H), 6.52(bs, 1H). |
| 77 | 1.00(t, 6H), 2.30(m, 1H), 2.95(s, 3H), 3.80(s, 3H), 4.74(m, 1H), 6.42(bs, 1H). |
| 78 | 1.69(s, 6H), 2.90(s, 3H), 3.81(s, 3H), 6.79(bs, 1H). |

General formula (I-2)

TABLE 3

General formula (I-2)

(I-2)

| No. | R¹ | Xn | Properties |
|---|---|---|---|
| 106 | CH₃ | H | m.p. 156° C. |
| 107 | CH₃ | 5-F | m.p. 176–177° C. |
| 108 | CH₃ | 6-F | m.p. 151° C. |
| 109 | CH₃ | 5-CH₃ | m.p. 193° C. |
| 110 | CH₃ | 8-CH₃ | m.p. 174° C. |
| 111 | C₂H₅ | H | m.p. 99° C. |
| 112 | i-C₃H₇ | H | m.p. 145° C. |

Next, typical examples of the compounds exhibiting a fungicidal activity against plant diseases which can be used in the form of a mixture with the 1,2,3-thiadiazole derivatives represented by the general formula (I) (hereinafter, these compounds are referred to as "Compound Group I") are shown below. The present invention is by no means limited thereby.

As the compounds exhibiting a fungicidal activity, the following can be referred to, for instance: melanin synthesis inhibitors (for example, the following compounds (2), (8), (7) and (10)); strobilurins type fungicides (for example, the following compounds (3) and (6)); ergosterol biosynthesis inhibitors (for example, the following compounds (4), (22), (23), (24), (25), (26) and (36)); acid amide type fungicides (for example, the following compounds (13), (14), (15), (16) and (17)); succinic acid synthetase inhibitor type fungicides; acylalanine type fungicides (for example, the following compound (27)); dicarboxyimide type fungicides (for example, the following compounds (39) and (40)); benzimidazole type fungicides (for example, the following compounds (41), (42) and (43)); dithiocarbamate type fungicides (for example, the following compounds (30), (31), (32) and (33)); metal-containing fungicides (for example, the following compounds (5), (28) and (29)); antibiotics (for example, the following compounds (9), (18) and (38)); etc.

Specific examples of the compounds exhibiting a fungicidal activity against plant diseases which can be used as a mixed ingredient in the composition of the present invention are listed below:

(1) Diisopropyl-1,3-dithiolan-2-ylidene malonate (general name: isoprothiolane)
(2) 5-Methyl-1,2,4-triazolo[3,4-b]benzothiazole (general name: tricyclazole)
(3) Methyl (E)-2-{2-[6-(2-cyanophenoxy)pyrimidin-4-yloxy]phenyl}-3-methoxyacrylate (general name: azoxystrobin)
(4) 1-[2-(2,4-dichlorophenyl)-4-propyl-1,3-dioxolan-2-ylmethyl]-1H-1,2,4-triazole (general name: propiconazole)
(5) 8-Hydroxyquinoline copper (general name: oxine-copper)
(6) 2-Methoxyimino-N-methyl-2-(2-phenoxy)phenyl-acetamide (code name: SSF-126)
(7) N-[1-(4-chlorophenyl(ethyl)-2,2-dichloro-1-ethyl-3-methylcyclopropanecarboxamide (general name: carpropamide)
(8) 4,5,6,7-Tetrachlorophthalide (general name: fthalide)
(9) Kasugamycin (general name: kasugamycin)
(10) 1,2,5,6-Tetrahydropyrrolo(3,2,1-i,j)quinolin-4-one (general name: pyroquilon)
(11) 3-Allyloxy-1,2-benzothiazole-1,1-dioxide (general name: probenazole)
(12) S-Methylbenzo-1,2,3-thiadiazole-7-carbothiolate (code name: CGA-245704)
(13) α, α, α-Trifluoro-3'-isopropoxy-o-toluanilide (general name: flutolanil)
(14) 3'-Isopropoxy-2-methylbenzanilide (general name: mepronil)
(15) 5-Chloro-1,3-dimethyl-N-(1,1-dimethyl-2-oxa-4-indanyl)pyrazole-4-carboxamide (general name: furametpyr)
(16) 1-(4-Chlorobenzyl)-1-cyclopentyl-3-phenylurea (general name: pencycuron)
(17) N-(2,6-Dibromo-4-trifluoromethoxyphenyl)-2-methyl-4-trifluoromethylthiazole-5-carboxamide (general name: thifluzamide)
(18) Validamycin (general name: validamycin)
(19) 6-(3,5-Dichloro-4-methylphenyl)-3(2H)pyridazinone (general name: diclomezine)
(20) (Z)-2'-Methylacetophenone=4,6-dimethyl pyrimidin-2-ylhydrazone (general name: ferimzone)
(21) 1,1'-Iminiodi (octamethylene) diguanidium=triacetate (general name: guazatine)
(22) 2-p-Chlorophenyl-2-(1H-1,2,4-triazol-1-ylmethyl) hexanenitrile (general name: myclobutanil)
(23) (RS)-2-(2,4-Dichlorophenyl)-1-(1H-1,2,4-triazol-1-yl) hexan-2-ol (general name: hexaconazole)
(24) 1-(4-Chlorophenoxy)-3,3-dimethyl-1-(1,2,4-triazol-1-yl)-2-butanone (general name: triadimefon)
(25) N-Propyl-N-[2-(2,4,6-trichlorophenoxy)ethyl]-imidazole-1-carboxamide (general name: prochloraz)
(26) cis-4-[3-(4-tert-butylphenyl)-2-methylpropyl]-2,6-dimethylmorpholine (general name: fenpropimorph)
(27) Methyl=N-(2-methoxyacetyl)-N-(2,6-xylyl)-DL-alaninate (general name: methalaxyl)
(28) Basic copper chloride (copper oxychloride)
(29) Basic copper sulfate (basic copper sulfate)
(30) Zinc ion-coordinated manganese ethylenebis-dithiocarbamate (general name: mancozeb)
(31) Zinc propylenebisdithiocarbamate (general name: propineb)
(32) Zinc dimethyldithiocarbamate (general name: ziram)
(33) Bis(dimethylthiocarbamoyl) disulfide (general name: thiram)
(34) 1-(2-Cyano-2-methoxyiminoacetyl)-3-ethylurea (general name: cymoxanil)
(35) Tetrachloroisophthalonitrile (general name: chlorothalonil)
(36) cis-trans-3-Chloro-4-[4-methyl-2-(1H-1,2,4-triazol-1-ylmethyl)-1,3-dioxolan-2-yl]phenyl=4-chlorophenyl= ether (general name: difenoconazole)
(37) N-trichloromethylthiotetrahydrophthalimide (general name: captan)
(38) Polyoxin (general name: polyoxin)
(39) 3-(3,5-Dichlorophenyl)-N-isopropyl-2,4-dioxoimidazolidine-1-carboxamide (general name: iprodione)
(40) N-(3,5-Dichlorophenyl)-1,2-dimethylcyclopropane-1,2-dicarboximide (general name: procymidone)
(41) Methyl 1-(butylcarbamoyl)-2-benzimidazole-carbamate (general name: benomyl)
(42) 1,2-Bis(3-methoxycarbonyl-2-thioureido)benzene (general name: thiophanate-methyl)
(43) 2-(Methoxycarbonylamino)benzimidazole (general name: carbendazin)
(44) Aluminum=tris(ethylphosphonate) (general name: fosetyl)
(45) 3-Hydroxy-5-methylisoxazole (general name: hymexazol)
(46) 5-Ethyl-5,8-dihydro-8-oxo[1,3]dioxolo[4,5-g]-quinoline-7-carboxylic acid (general name: oxolinic acid)
(47) 4-(2,2-Difluoro-1,3-benzodioxol-4-yl)pyrrole-3-carbonitrile (general name: fludioxonil)
(48) N-(4-Methyl-propa-1-ynylpyrimidin-2-yl)aniline (general name: mepanipyrim)
(49) 4-Cyclopropyl-6-methyl-N-phenylpyrimidine-2-amine (general name: cyprodinil)
(50) N-(4,6-Dimethylpyrimidin-2-yl)aniline (general name: pyrimethanil)
(51) O-2,6-Dichloro-p-tolyl O,O-dimethyl-phosphorothioate (general name: tolclofos-methyl)
(52) Mixture at arbitrary proportions of N-(1-cyano-1,2-dimethylpropyl)-2-(2,4-dichlorophenoxy)-propaneamide or optically active compounds thereof or isomers thereof (the compounds disclosed in JP-A-63-132867), and the like. These compounds can be used either alone or in the form of a mixture of two or more compounds.

The plant disease controlling composition of the present invention obtained by combining a 1,2,3-thiadiazole derivative represented by the general formula (I) or a salt thereof with at least one compound selected from the Compound Group I exhibits an excellent controlling effect against the plant diseases exemplified below. Further, the composition of the invention exercises an effect also against the fungi resistant to the existing fungicidal agents.

Roughly saying, the plant diseases on which the composition exhibits an effect are classified into mold fungi diseases, bacterial diseases and viral diseases. For instance, there are included the diseases due to Deuteromycetes such as Genus Botrytis, Genus Helminthosporium, Genus Fusarium, Genus Septoria, Genus Cercospora, Genus Pyricularia and Genus Alternaria, the diseases due to Basidiomycetes such as Genus Hemileia, Genus Rhizoctonia and Genus Puccinia, the diseases due to Ascomycetes such as Genus Venturia, Genus Podosphaera, Genus Erysiphe, Genus Monilinia and Genus Unsinula, the diseases due to the other fungi such as Genus Ascochyta, Genus Phoma, Genus Pythium, Genus Corticium and Genus Pyrenophora, the diseases due to bacteria such as Genus Pseudomonas, Genus Xanthomonas and Genus Erwinia, and the diseases due to viruses such as tobacco mosaic virus.

Specific examples of the diseases against which the composition of the present invention exhibit a marked effect include rice blast (*Pyricularia oryzae*), rice sheath blight (*Rhizoctonia solani*), rice Helminthosporium leaf spot (*Cochliobolus miyabeanus*), rice seedling blight (*Rhizopus chinensis, Pythium graminicola, Fusarium graminicola, Fusarium roseum*, Mucor sp., Phoma sp., Tricoderma sp. ), rice bakanae disease (*Gibberella fujikuroi*), powdery mildew of barley and wheat (*Erysiphe graminis*), powdery mildew of cucumber (*Sphaerotheca fuliginea*), powdery mildew of other host plants, eye spot of barley and wheat (*Pseudocercosporella herpotrichoides*), flag smut of wheat, etc. (*Urocystis tritici*), snow mold of barley and wheat (*Fusarium nivale, Pythium iwayamai, Typhla ishikariensis, Sclerotinia boreasis*), oats crown rust (*Puccinia coronata*), stem rust of other plants, gray mold of cucumber and strawberry (*Botrytis cinerea*), sclerotinia rot of tomato and cabbage (*Sclerotinia sclerotiorum*), late blight of potato and tomato (*Phytophthora infestans*), Phytophthora rot of other plants, downy mildew of various plants such as cucumber downy mildew (*Pseudoperonospora cubensis*), grape downy mildew (*Plasmopara viticola*), etc., apple scab (*Venturia inaequalis*), apple Alternaria leaf spot (*Alternaria mali*), pear black spot (*Alternaria kikuchiana*), citrus melanose (*Diaporthe citri*), citrus scab (*Elsinoe fawcetti*), sugar beet Cercospora leaf spot (*Cercospora beticola*), peanut brown leaf spot (*Cercospora arachidicola*), peanut leaf spot (*Cercospora personata*), septoria leaf spot of wheat (*Septoria tritici*), glume blotch of wheat (*Septoria nodorum*), scald of barley (*Rhynchosporium secalis*), bunt of wheat (*Tilletia caries*), lawn grass brown patch (*Rhizoctonia solani*), lawn grass dollar spot of lawn grass (*Sclerotinia homoeocarpe*); bacterial diseases due to Genus Pseudomonas such as cucumber bacterial blight (*Pseudomonas syringae pv. lachrymans*), tomato bacterial wilt (*Pseudomonas solanacearum*) and rice glume blight (*Pseudomonas glumae*), bacterial diseases due to Genus Xanthomonas such as cabbage black rot (*Xanthomonas campestris*), rice bacterial leaf blight (*Xanthomonas oryzae*) and citrus canker (*Xanthomonas citri*), and bacterial diseases due to Genus Erwinia such as cabbage bacterial soft rot (*Erwinia carotovora*), and viral diseases such as tobacco mosaic (tobacco mosaic virus), etc.

The plants to which the fungicidal composition of the present invention can be applied are not particularly limited, and the following plants can be referred to as examples thereof:

cereals such as rice, barley, wheat, rye, oat, corn, kaoliang, etc.; beans and peas such as soybean, red bean, broad bean, pea, peanut, etc.; fruit trees and fruits such as apple, citrus trees and fruits, pear, grape, peach, plum, cherry, walnut, almond, banana, strawberry, etc.; vegetables such as cabbage, tomato, spinach, broccoli, lettuce, onion, stone-leek, Spanish paprika, etc., root crops such as carrot, potato, sweet potato, radish, lotus rhizome, turnip, etc.; processing crops such as cotton, flax, paper mulberry, mitsumata, rape seed plant, beet, hop, sugar cane, sugar beet, olive, gum, coffee, tobacco, tea, etc.; cucurbitaceous plants such as pumpkin, cucumber, water melon, melon, etc.; pasture plants such as orchard grass, sorghum, timothy, clover, alfalfa, etc.; lawn grasses such as mascarenegrass, bent grass, etc.; perfumery crops such as lavender, rosemary, thyme, parsley, pepper, ginger, etc.; and flower plants such as chrysanthemum, rose, orchid, etc.

In order to control various diseases, the fungicidal composition of the present invention is put to use either as it is or in the form of a dilution or a suspension in a proper quantity of water or the like by applying a quantity for effectively exhibiting the plant disease controlling effect to the plant on which an occurrence of the disease is expected or a site at which occurence of the disease is to be prevented. For instance, with the aim of controlling the disease of paddy field rice plant, it may be applied to paddy field water or boxes for raising rice seedlings, or by the method of seed coating, seed soaking or the like. Against the diseases occurring in the upland field of fruit plants, cereals, vegetables, etc., not only the treatment of leaves and stalks but also immersion of seeds in the agent solution, treatment of seeds with powdery agent or treatment of soil aiming at absorption from the roots can also be adopted. It may also be used for treatment of water culture solution for use in water cultures.

As the method of treating seeds, a method of dipping seeds in a diluted or undiluted liquid preparation and thereby making the agent permeate into the seeds, a method of mixing a solid or liquid preparation with seeds for the sake of powder coating and thereby making the agent adhere to the seed surface, a method of mixing the preparation with an adhesive carrier such as resin, polymer or the like and coating seeds with such an adhesive mixture, a method of spraying the preparation to the neighborhood of seeds simultaneously with planting, etc. can be referred to.

The term "seed" to be treated with the composition of the present invention means a plant body of the initial stage of cultivation used for reproduction of plants, and involves not only the so-called seeds but also plant bodies for nutrient reproduction such as bulb, tuber, seed tuber, aerial tuber, scaly bulb, stalks for cuttage, and the like.

The term "soil" or "cultivation carrier" for plants in the practice of the using method of the present invention means a support for use in culture of a plant and especially a support in which roots are to be grown. They are not limited in material quality, but any material may be used so far as a plant can be grown therein. For instance, so-called various soils, seedling mat, water and the like can also be used. Specific examples of the material constituting the soil or cultivation carrier include sand, vermiculite, cotton, paper, diatomaceous earth, agar, gelatinous materials, polymeric materials, rock wool, glass wool, wood chips, bark, pumice and the like.

As method for spraying the composition to the stalks and leaves, a method of diluting a liquid preparation such as emulsifiable concentrate, flowable agent or a solid preparation such as wettable powder or wettable granular composition with a proper quantity of water and then spraying the dilution to leaves and stalks and a method of spraying the powdery composition can be referred to.

As method for applying the composition to the soil, a method of applying a liquid preparation either diluted or undiluted with water to the base of stalks, seedling bed for raising seedlings or the like, a method of spraying a granular agent to the stalk base or seedling bed, a method of spraying a dust, a wettable powder, a wettable granule or a granular agent to the soil and mixing it with the whole soil either before seeding or before transplantation, a method of spraying a dust, a wettable powder, a wettable granule, a granular agent or the like to planting holes, planting rows, etc. can be referred to.

For applying the fungicide of the present invention to a seedling box of paddyfield riceplant, the fungicide may be applied in the form of a dust, a wettable granular composition or a granular composition, though the preparation form may be dependent on the time of application or whether it is applied at the seeding time, in the greening period or at the time of transplantation. Otherwise, the fungicide may also be applied by mixing it into a molding. A molding may be mixed with a dust, a wettable granule or a granular composition by the method of bed soil mixing, covering soil mixing or mixing into the whole mold. It is also possible to form alternating layers of molding and fungicidal composition. When the fungicide is applied at the seeding time, the time of application of the fungicide may be any of before the seeding, simultaneous with the seeding and after the seeding, or it also be after coverage of soil.

For applying the fungicide to paddy field, a solid preparation such as jumbo-pack, granule, wettable granule and the like or a liquid preparation such as flowable, emulsifiable concentrate and the like is scattered to a paddy field usually in a submerged state. Otherwise, it is also possible to scatter or inject an appropriate agent as it is or its mixture with fertilizers into soil at the time of transplantation of rice seedlings. It is further possible to apply an emulsifiable concentrate, a wettable powder or a flowable preparation to the water inlet or water flow source of irrigating apparatus, by which the fungicide can be applied together with water supplied to the paddy field in a labor-saving manner.

In case of upland field crops such as wheat, a fungicidal composition may be applied to the cultivation carrier surrounding the seeds or plant bodies in the period from the seeding to the seedling raising. In cases where plant seeds are directly sown to the field, the fungicide may directly be applied to the seeds to make seed coating, or may also be applied to the base of hills to achieve a successful result. It is also possible to scatter a granular preparation, or to apply a liquid preparation after being diluted with water or without dilution.

In cases where cultured plants to be transplanted are treated at the seeding time or in the seedling raising period, preferable are a direct treatment of seeds, an irrigating treatment using a liquefied agent or a powdering treatment of granular agent to the seedling-raising bed. Further, application of granular agent to the planting holes at the time of set-planting and mixing of a fungicide into the cultivation carrier in the neighborhood of the sites of transplantation are also preferable.

As for the dosage of the active ingredient compound of the plant disease controlling composition of the present invention, at least one compound properly selected from the Compound Group I is used usually in an amount of 0.01-1,000 parts by weight and preferably 0.1 to 100 parts by weight, per part by weight of the 1,2,3-thiadiazole derivative of general formula (I) or a salt thereof.

The plant disease controlling composition of the present invention may be applied in a preparation form of, for instance, emulsifiable concentrate, wettable powder, suspension, solution, granule, dust or the like. Although the dosage thereof varies depending on the content of active ingredient in the composition, climate conditions, preparation form, time of application, method of application, place of application, disease to be controlled and objective crop plant, the dosage is appropriately selected usually from a range of 0.1-1,000 grams and preferably 1-50 grams as expressed in terms of weight of active ingredient, per are of the field. In the case of seed treatment, the weight of active ingredient may be changed in the range of 0.01-40% based on the seed. When emulsifiable concentrate, wettable powder, suspension or solution is diluted with water and then put to use, the concentration at the time of application is 0.0001-0.1%. In the cases of a granular composition, a dust composition and a liquid composition to be used for seed treatment, the compositions may directly be put to use without dilution.

EXAMPLE

Next, typical examples and test examples of the present invention are presented below. The invention is by no means limited by these examples. In the examples, the term "part" means part by weight.

Example 1

| The compound of Table 1 or 3 | 10 parts |
| One compound of Compound Group I | 10 parts |
| Calcined diatomaceous earth | 63 parts |
| Polyoxyethylene nonylphenyl ether | 5 parts |
| Naphthalenesulfonic acid-formaldehyde condensate | 4 parts |
| Silicic acid hydrate | 8 parts |

A wettable powder is prepared by uniformly mixing and grinding the ingredients mentioned above.

Example 2

| Compound of Table 1 or 3 | 10 parts |
| One compound of Compound Group I | 35 parts |
| Calcined diatomaceous earth | 28 parts |
| Polyoxyethylene nonylphenyl ether | 5 parts |
| Naphthalenesulfonic acid-formaldehyde condensate | 4 parts |
| Silicic acid hydrate | 8 parts |

A wettable powder is prepared by uniformly mixing and grinding the ingredients mentioned above.

Example 3

| Compound of Table 1 or 3 | 40 parts |
| One compound of Compound Group I | 10 parts |
| Calcined diatomaceous earth | 33 parts |
| Polyoxyethylene nonylphenyl ether | 5 parts |
| Naphthalenesulfonic acid-formaldehyde condensate | 4 parts |
| Silicic acid hydrate | 8 parts |

A wettable powder is prepared by uniformly mixing and grinding the ingredients mentioned above.

Example 4

| | |
|---|---|
| Compound of Table 1 or 2 | 5 parts |
| One compound of Compound Group I | 7 parts |
| Synthetic silicic acid hydrate | 1 part |
| Calcium ligninsulfonate | 2 parts |
| Bentonite | 30 parts |
| Kaolin clay | 55 parts |

A granular composition is prepared by uniformly mixing and grinding the ingredients mentioned above, adding an appropriate quantity of water, and kneading and drying the resulting mixture.

Example 5

| | |
|---|---|
| Compound of Table 1 or 3 | 20 parts |
| One compound of Compound Group I | 20 parts |
| Sodium alkylnaphthalenesulfonate | 3 parts |
| Propylene glycol | 5 parts |
| Dimethylpolysiloxane | 0.25 part |
| p-Chloro-m-xylenol | 0.10 part |
| Xanthane gum | 0.30 part |
| Water | 51.35 parts |

A wettable powder or an aqueous suspension is prepared by uniformly mixing and grinding the ingredients mentioned above.

Test Example 1

Preventive Effect on Rice Blast by Spraying

A wettable powder prepared according to the examples mentioned above and diluted with water to a predetermined concentration was sprayed to stalks and leaves of rice plants (variety: Kimmaze) of 6-leaved stage cultivated in pots. After the spraying, the pots were cultivated in a greenhouse. Seven days after the treatment, the plants were inoculated with a spore suspension of rice blast fungi (*Pyricularia oryzae*) by the method of spraying.

After the inoculation, the plants were left to stand for 7 days at 20° C. under a high humidity condition, and then the number of lesions was counted, from which controlling degree was calculated according to the equation mentioned below. In the-untreated-plot, the number of lesions was 23.0 per leaf.

$$\text{Controlling degree (\%)} = \frac{\text{Number of lesions in untreated plot} - \text{Number of lesions in treated plot}}{\text{Number of lesions in untreated plot}} \times 100$$

Further, the theoretically expected controlling degree was calculated according to the following formula:

Theoretically expected controlling degree $(\%) = X + (100-X) \times Y/100$ wherein X is controlling degree (%) of agent A at 12.5 ppm and Y is controlling degree (%) of agent B at 12.5 ppm (the portion which could not be controlled with agent A corresponded to (100−X)%, of which Y%, namely (100−X)×Y/100, was controlled by agent B.

The results are shown in Table 4.

TABLE 4

| Test agent | Concentration (ppm) | Actual controlling degree (%) | Theoretical controlling degree (%) |
|---|---|---|---|
| Compound No. 3 + Isoprothiolane | 12.5 + 12.5 | 64 | 42 |
| Compound No. 3 + Tricyclazole | 12.5 + 12.5 | 70 | 43 |
| Compound No. 3 | 12.5 | 27 | |
| Isoprothiolane | 12.5 | 20 | |
| Tricyclazole | 12.5 | 22 | |

Test Example 2

Preventive Effect on Barley Powdery Mildew by Spraying

A wettable powder prepared according to the examples mentioned above and diluted to a predetermined concentration was applied to stalks and leaves of barley plant (variety: Kanto No. 6) of 2-leaved stage cultivated in pots. After the spraying, the pots were cultivated in a greenhouse. Seven days after the treatment, the plants were inoculated with spores of powdery mildew (*Erysiphe graminis*) by the method of powdering. Seven days after the inoculation, the number of lesions was counted, from which controlling degree was calculated according to Test Example 1. In the untreated plot, the number of lesions was 17.7 per leaf. The theoretical controlling degree was calculated in the same manner as in Test Example 1.

The results are shown in Table 5.

TABLE 5

| Test agent | Concentration (ppm) | Actual controlling degree (%) | Theoretical controlling degree (%) |
|---|---|---|---|
| Compound No. 3 + Azoxystrobin | 20 + 20 | 87 | 66 |
| Compound No. 3 + Propiconazole | 20 + 20 | 85 | 67 |
| Compound No. 3 | 20 | 15 | |
| Azoxystrobin | 20 | 60 | |
| Propiconazole | 20 | 63 | |

Test Example 3

Preventive Effect on Cucumber Downy Mildew by Spraying

A wettable powder prepared according to the examples mentioned above was diluted with water to a predetermined concentration and sprayed to stalks and leaves of cucumber (variety: Suyo) of 2.5-leaved stage cultivated in pots. After the spraying, the pots were cultivated in a greenhouse. Six days after the treatment, the plants were inoculated with zoospores of downy mildew (*Pseudoperonospora cubensis*). Seven days after the inoculation, the plants were examined and the disease occurrence index was determined according to the criterion shown below, from which controlling degree was calculated according to the following equation. In the untreated plot, the disease occurrence index was 7.8. The theoretical controlling degree was calculated in the same manner as in Test Example 1.

Disease Occurrence Index

0: No occurrence of disease
1: Areal rate of lesion: 1–10%
2: Areal rate of lesion: 11–20%
3: Areal rate of lesion: 21–30%
4: Areal rate of lesion: 31–40%
5: Areal rate of lesion: 41–50%
6: Areal rate of lesion: 51–60%
7: Areal rate of lesion: 61–70%
8: Areal rate of lesion: 71–80%
9: Areal rate of lesion: 81–90%
10: Areal rate of lesion: 91–100%

Controlling degree (%) =

$$\frac{\text{Disease occurrence index in untreated plot} - \text{Disease occurrence index in treated plot}}{\text{Disease occurrence index in untreated plot}} \times 100$$

The results are shown in Table 6.

TABLE 6

| Test agent | Concentration (ppm) | Controlling degree (%) | Theoretical controlling degree (%) |
|---|---|---|---|
| Compound NO. 3 + 8-Hydroxyquinoline-copper | 50 + 50 | 75 | 60 |
| Compound No. 3 | 50 | 20 | |
| 8-Hydroxyquinoline-copper | 50 | 50 | |

Test Example 4

Control Test on Cabbage Black Rot

A wettable powder composition prepared according to the examples mentioned above was diluted with water to a predetermined concentration and sprayed to cabbage (variety: Kinkei No. 201) of early head forming period four times at intervals of 7 days of 280 liters per 10 ares. Two days after the second spraying, the cabbage was inoculated with an aqueous suspension of cabbage black rot bacterium (*Xanthomonas campestris*) by the method of spraying. Two weeks after the final spraying, the cabbage was investigated to calculated the degree of disease occurrence according to the following criterion. In the untreated plot, the degree of disease occurrence was 44.7. Theoretical controlling degree was calculated in the same manner as in Test Example 1.

Degree of disease occurrence=Σ(Number of hills at every degree of occurrence)×100÷(Number of hills investigated×3)

| Index | State of disease occurrence |
|---|---|
| 0: | No occurrence of disease or only very slight number of lesions |
| 1: | Lesions are sporadically found on a few outer leaves. |
| 2: | Rather many lesions are found on all the outer leaves. |
| 3: | Many lesions are found on all the outer leaves, and some of the heads are diseased. |

From the degree of disease occurrence, controlling degree was calculated according to the following equation. Theoretical controlling degree was calculated in the same manner as in Test Example 1.

$$\text{Controlling degree (\%)} = \frac{\text{degree of disease occurence in untreated plot} - \text{degree of disease occurence in treated plot}}{\text{Degree of disease occurence in untreated plot}} \times 100$$

The results are shown in Table 7.

TABLE 7

| Test agent | Concentration (ppm) | Percentage of diseased hills (%) | Degree of disease occurrence | Controlling degreee (%) | Theoretical controlling degree (%) |
|---|---|---|---|---|---|
| Compound No. 3 + 8-Hydroxyquinoline-copper | 100 + 350 | 27.0 | 9.0 | 80 | 59 |
| compound No. 3 | 100 | 98.2 | 52.8 | 0 | |
| 8-Hydroxyquinoline-copper | 350 | 54.5 | 18.2 | 59 | |

Test Example 5

Controlling Test on Cucumber Bacterial Blight

A wettable powder composition prepared according to the examples mentioned above was diluted with water to a predetermined concentration and sprayed to cucumber (variety: Topgreen) of growth period three times, at intervals of 7 days of 280 liters per 10 ares. Six hours after the first spraying, the cucumber was inoculated with an aqueous suspension of cucumber bacterial blight bacterium (*Pseudomonas syringae pv. lachrymans*) by the method of spraying. One week after the final spraying, the cucumber was investigated to calculated the degree of disease occurrence according to the following criterion. In the untreated plot, the degree of disease occurrence was 63.9. Theoretical controlling degree was calculated in the same manner as in Test Example 1.

Degree of disease occurrence=Σ(Number of diseased leaves at every degree of disease occurrence×index)×100÷(Number of hills investigated×4)

| Index | State of disease occurrence |
|---|---|
| 0: | No disease occurrence |
| 1: | Areal rate of disease occurrence: less than 5% |
| 2: | Areal rate of disease occurrence: no less than 5% and less than 25% |
| 3: | Areal rate of disease occurrence: no less than 25% and less than 50% |
| 4: | Areal rate of disease occurrence: no less than 50%. |

From the degree of disease occurrence, controlling degree was calculated according to Test Example 4. The theoretical controlling degree was calculated in the same manner as in Test Example 1.

The results are shown in Table 8.

TABLE 8

| Test agent | Concentration (ppm) | Percentage of diseased leaves (%) | Controlling degree (%) | Theoretical controlling degree (%) |
|---|---|---|---|---|
| Compound 3 + 8-Hydroxyquinoline-copper | 100 + 350 | 33.3 | 67 | 47 |
| Compound 3 | 100 | 53.9 | 46 | |
| 8-Hydroxyquinoline-copper | 350 | 99.4 | 1 | |

Test Example 6

Controlling Test on Wheat Powdery Mildew

A wettable powder prepared according to the examples mentioned above was applied to wheat in the internode elongation period of 100 liters per 10 ares. Two months after the chemical treatment, areal rate of lesion on the flag leaves was measured, from which controlling degree was calculated according to the following equation. In the untreated plot, the areal rate of lesion was 15%. The theoretical controlling degree was calculated in the same manner as in Test Example 1.

$$\text{Controlling degree (\%)} = \frac{\text{Areal rate of lesion in untreated plot} - \text{Areal rate of lesion in treated plot}}{\text{Area rate of lesion in untreated plot}} \times 100$$

The results are shown in Table 9.

TABLE 9

| Test agent | Dosage (ppm) | Controlling degree (%) | Theoretical controlling degree (%) |
|---|---|---|---|
| Compound No. 3 + Azoxystrobin | 200 + 100 | 83 | 56 |
| Compound No. 55 + Azoxystrobin | 200 + 100 | 70 | 44 |

TABLE 9-continued

| Test agent | Dosage (ppm) | Controlling degree (%) | Theoretical controlling degree (%) |
|---|---|---|---|
| Compound No. 3 | 200 | 27 | |
| Compound No. 55 | 200 | 7 | |
| Azoxystrobin | 100 | 40 | |

Test Example 7

Controlling Test on Tobacco Mosaic Virus Disease

A wettable powder prepared according to the examples mentioned above was diluted with water to a predetermined concentration, and sprayed to a tobacco plant of 5-leaved stage (variety: Samson NN). Seven days after the chemical treatment, the tobacco leaves, previously powdered with 60 mesh Carborundum, was inoculated by lightly patting the leaf surface with cotton applicator immersed in a 10 μg/ml solution of tobacco mosaic virus in phosphate buffer (pH 6.8). Just after the inoculation, the Carborundum was washed away with running water, and the plant was left to stand in a greenhouse until local lesions were formed. Then, diameters of lesions were measured, from which controlling degree was calculated according to the following equation. In the untreated plot, diameter of the lesion was 2.2 mm. The theoretical controlling degree was calculated in the same manner as in Test Example 1.

$$\text{Controlling degree (\%)} = \frac{\text{Diameter of lesion in untreated plot} - \text{Diameter of lrdin in treated plot}}{\text{Diameter of lesion in untreated plot}} \times 100$$

The results are shown in Table 10.

TABLE 10

| Test agent | Dosage (ppm) | Controlling degree (%) | Theoretical controlling degree (%) |
|---|---|---|---|
| Compound No. 3 + Isoprothiolane | 200 + 200 | 35 | 20 |
| Compound No. 3 | 200 | 20 | |
| Isoprothiolane | 200 | 0 | |

Test Example 8

Controlling Effect on Rice Bakanae Disease by Seed Coating Treatment

Unhulled rice seeds (variety: Kimmaze) infected with rice bakanae disease fungi (*Gibberella fujikuroi*) were subjected to a powder coating treatment by introducing the rice seeds into a vinyl bag together with a wettable powder prepared according to the examples mentioned above and thoroughly mixing them together with a small quantity of water. After the treatment, the unhulled rice was air-dried overnight, immersed in water at 15° C. for one week, and then kept at 30° C. to promote germination, after which the unhulled rice seeds were sown in a seedling raising box, germination thereof was hastened at 30C for 3 days, and the plants were cultivated in a greenhouse for about one month. Then, the diseased seedling rate was investigated, from which the controlling degree was calculated according to the following equation. In the untreated plot, the diseased seedling rate was 78%. The theoretical controlling degree was calculated in the same manner as in Test Example 1. The results are shown in Table 11.

$$\text{Controlling degree (\%)} = \frac{\text{Diseased seedling rate in untreated plot} - \text{Disease seedling rate in treated plot}}{\text{Diseased seedling rate in untreated plot}} \times 100$$

The results are shown in Table 11.

TABLE 11

| Test agent | Dosage (wt. % of active ingredient per dry unhulled rice) (%) | Controlling degree (%) | Theoretical controlling degree (%) |
|---|---|---|---|
| Compound NO. 55 + Oxolinic acid | 0.2 + 0.2 | 75 | 45 |
| Compound No. 55 | 0.2 | 45 | |
| Oxolinic acid | 0.2 | 0 | |

Test Example 9

Controlling Effect on Cucumber Downy Mildew by Soil Mixing Treatment

A wettable powder prepared according to the examples mentioned above was mixed into soil, and the soil thus obtained was filled into pots so that one pot contained 5 g of the wettable powder. Then, cucumber (variety: Suyo) seedlings of cotyledon-developing period were transplanted into the pots. After cultivating the pots in a greenhouse for 2 weeks, the plants were inoculated with zoospores of downy mildew (*Pseudoperonospora cubensis*). Seven days after the inoculation, the plants were investigated and evaluated according to Test Example 3, from which controlling degree was determined. In the untreated plot, the disease occurrence index was 6.5. The theoretical controlling degree was calculated in the same manner as in Test Example 1.

The results are shown in Table 12.

TABLE 12

| Test agent | Dosage (amt. of active ingredient per pot) (g) | Theoretical Controlling degree (%) | controlling degree (%) |
|---|---|---|---|
| Compound No. 55 + Benomyl | 0.1 + 0.1 | 72 | 41 |
| Compound No. 55 | 0.1 | 40 | |
| Benomyl | 0.1 | 2 | |

Test Example 10

Controlling Effect on Wheat Powdery Mildew by Seed Coating Treatment

Seeds of wheat (variety: Chihoku) and a wettable powder prepared according to the examples mentioned above were introduced into a vinyl bag. A small quantity of water was added thereto and thoroughly mixed together to carry out a seed coating treatment. After the treatment, the seeds were air-dried overnight, sown in pots, and cultivated in a greenhouse. One month after the seeding, the plants were inoculated with spores of powdery mildew (*Erysiphe graminis*) by the method of powdering. Seven days after the inoculation, the number of lesions was counted, from which controlling degree was calculated according to Test Example 1. In the untreated plot, the number of lesions per leaf was 25. The theoretical controlling degree was calculated in the same manner as in Test Example 1.

When only the compound formula (I) is used, the result of seed treatment is superior to the result of spraying to stalks and leaves in course of cultivation (for instance, Test Example 2 and Test Example 6) in terms of dosage per area of cultivation. Further, when the mixed agent according to the present invention is used for the seed treatment, the activity is more enhanced, and the effect exhibited is far more excellent than that achieved by spraying a single agent.

TABLE 13

| Test agent | Dosage (amt. of active ingredient per dry seed weight) (%) | Controlling degree (%) | Theoretical controlling degree (%) |
|---|---|---|---|
| Compound No. 55 + Benomyl | 1 + 1 | 96 | 88 |
| Compound No. 55 | 1 | 88 | |
| Benomyl | 1 | 0 | |

What is claimed is:

1. A fungicidal composition comprising a fungicidally effective amount of a 1,2,3-thiadiazole compound of the following structure:

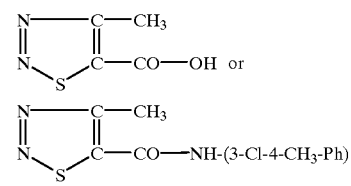

and a compound having fungicidal activity selected from the group consisting of isoprothiolane, tricyclazole, azoxystrobin, propiconazole, 8-hydroxyquinoline-copper, oxolinic acid and benomyl.

2. The fungicidal composition of claim 1 comprising a fungicidally effective amount of a 1,2,3-thiadiazole compound of the following structure,

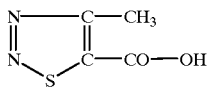

and a compound having fungicidal activity selected from the group consisting of isoprothiolane, tricyclazole, azoxystrobin, propiconazole, and 8-hydroxyquinoline-copper.

3. The fungicidal composition of claim 1 comprising a fungicidally effective amount of a 1,2,3-thiadiazole compound of the following structure,

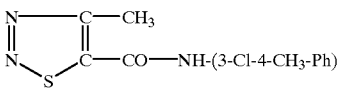

and a compound having fungicidal activity selected from the group consisting of azoxystrobin, oxolinic acid and benomyl.

* * * * *